United States Patent
Pradel

(10) Patent No.: US 8,304,713 B2
(45) Date of Patent: *Nov. 6, 2012

(54) DEVICE AND METHOD FOR CALIBRATING A SENSOR SYSTEM

(75) Inventor: Helmut Pradel, München (DE)

(73) Assignee: Giesecke & Devrient GmbH, Munich (DE)

(*) Notice: Subject to any disclaimer, the term of this patent is extended or adjusted under 35 U.S.C. 154(b) by 164 days.

This patent is subject to a terminal disclaimer.

(21) Appl. No.: 12/673,622

(22) PCT Filed: Aug. 14, 2008

(86) PCT No.: PCT/EP2008/006712
§ 371 (c)(1),
(2), (4) Date: Feb. 16, 2010

(87) PCT Pub. No.: WO2009/021745
PCT Pub. Date: Feb. 19, 2009

(65) Prior Publication Data
US 2011/0031386 A1    Feb. 10, 2011

(30) Foreign Application Priority Data
Aug. 16, 2007  (DE) .................. 10 2007 038 753

(51) Int. Cl.
*G01D 18/00*    (2006.01)
(52) U.S. Cl. .................................................. 250/252.1
(58) Field of Classification Search ................ 250/252.1
See application file for complete search history.

(56) References Cited

U.S. PATENT DOCUMENTS

| 5,764,346 | A | 6/1998 | Jard et al. |
|---|---|---|---|
| 5,982,501 | A | 11/1999 | Benz et al. |
| 6,516,209 | B2 * | 2/2003 | Cheng et al. ............... 600/323 |
| 6,977,365 | B1 | 12/2005 | Wynn |
| 7,081,614 | B2 * | 7/2006 | Duncan et al. ............. 250/252.1 |
| 7,193,701 | B2 * | 3/2007 | Mark ........................ 356/243.1 |
| 2001/0008275 | A1 | 7/2001 | Yanagiuchi |
| 2006/0017922 | A1 | 1/2006 | Lewis et al. |
| 2006/0093522 | A1 | 5/2006 | Kormann et al. |
| 2006/0138344 | A1 | 6/2006 | Gunstream et al. |
| 2006/0214112 | A1 | 9/2006 | Resch-Genger et al. |
| 2007/0012885 | A1 | 1/2007 | Montagu |
| 2009/0302206 | A1 * | 12/2009 | Harris et al. ............... 250/252.1 |
| 2011/0148764 | A1 * | 6/2011 | Gao ........................... 345/163 |

FOREIGN PATENT DOCUMENTS

| DE | 102004021448 A1 | 11/2005 |
|---|---|---|
| DE | 102004044717 A1 | 3/2006 |
| EP | 0878704 A1 | 11/1998 |
| WO | WO 2005106431 A1 * | 11/2005 |
| WO | 2006025846 A1 | 3/2006 |
| WO | 2006035012 A1 | 4/2006 |

* cited by examiner

*Primary Examiner* — Christine Sung
(74) *Attorney, Agent, or Firm* — Bacon & Thomas, PLLC

(57) ABSTRACT

An apparatus for the calibration of a sensor system has at least one sensor and at least one excitation source, a control device for controlling the sensor system, a calibration medium and a drive which moves the calibration medium into an optical path of the sensor system in a calibration mode and moves the calibration medium out of the optical path of the sensor system in an operating mode for the testing of measuring objects. The calibration medium has more than one reference, where the drive moves the calibration medium into the optical path of the sensor system so that one of the references covers a detection area of the sensor system, and the sensor system measures the reference located in the detection area.

5 Claims, 2 Drawing Sheets

DEVICE AND METHOD FOR CALIBRATING A SENSOR SYSTEM

FIELD OF THE INVENTION

The invention relates to an apparatus and a method for the calibration of a sensor system.

BACKGROUND

In order to ensure a correct function of sensors, sensors usually are calibrated. For the calibration of sensors there are used calibration media which have certain, predetermined properties. By means of these known properties it is possible to calibrate the sensors, because the known properties of the calibration media have to yield certain, expected measuring signals of the sensors. Thus it is possible to recognize deviations of the sensors, which are caused by e.g. manufacturing, ageing, soiling etc, and to take these into account in measurements. For this purpose, in a calibration mode it is ascertained whether the measuring signals of the sensors deviate from the measuring signals expected due to the calibration medium. The size of the ascertained deviations determines the adjustments required for a correction of the deviations. For this purpose for example correction factors can be determined which are applied to the measuring signals of the sensors upon subsequent measurements in the operating mode in order to compensate for the deviations. Likewise, the intensity of an excitation source, for example an illumination, can be changed upon the correction until the measuring signals of the sensor have the expected values. The changed intensity of the excitation source is maintained and subsequently used for measurements with the sensor, thereby compensating for the occurred deviations.

Special difficulties will arise, if great demands are made on the calibration of sensors, because by means of the sensors there are carried out sensible measurements, e.g. the recognition of documents of value, in the following referred to as bank notes, whose type (currency, denomination), authenticity, state (soiling, damage) etc is to be ascertained. Such cases require a very precise calibration of the sensors, since misjudgments due to wrong measuring signals of the sensors must be absolutely avoided, so that besides a white balance, necessarily, a color balance must also be carried out in order to certainly avoid misjudgments. In this connection, the use of high-quality calibration media having standardized references, so-called measuring standards, has also turned out to be problematic for various reasons.

From WO 2006/025846 A1 there is known a self-calibrating optical system which uses a high-quality calibration medium having a standardized white reference which is integrated in a sensor housing of the optical system. The calibration medium having the standardized white reference is pivoted into the optical path of the sensor during the calibration mode by means of a mechanism within the sensor housing. Due to the defined optical properties of the standardized white reference a self-calibration of the sensor is possible at any time. In the operating mode the calibration medium is pivoted out of the optical path of the sensor by means of the mechanism, in order to permit measurements of e.g. pharmaceutical products. There is additionally proposed to use a further calibration medium which has certain spectral properties. For this further calibration medium there is also provided a further mechanism to permit the further calibration medium to be pivoted into and out of the optical path of the sensor within the sensor housing.

The self-calibrating optical system known from WO 2006/025846 A1, however, has the disadvantage that for each calibration medium to be used a separate mechanism must be used to permit the calibration media to be successively pivoted into and out of the optical path of the sensor, so that the latter can be calibrated by means of the calibration media having different properties, for example a white and color balance can be performed.

A further problem arises from the fact that high-quality calibration media having standardized references have to be used so as to penult the desired self-calibration at any time. The use of the standardized references on the one hand has the disadvantage that such standardized references have to be employed in each optical system to be calibrated, but such standardized references for the calibration are expensive. This results from the necessity to exactly measure the standardized references, since for the self-calibration it has to be ensured that the references exactly have the desired properties. On the other hand, despite the relatively protected accommodation of the standardized reference it may come to changes of the standardized reference e.g. due to ageing. In this case a reliable self-calibration of the sensor is no longer possible.

Furthermore, due to the accommodation of the calibration media having the standardized references within the sensor housing and the pivoting into the optical path of the sensor to be calibrated within the sensor housing there is always given a deviation from the actual measuring place of the sensor which is located outside the sensor housing. This problem is further aggravated, when the sensors or an associated illumination are to detect larger line-shaped or areal regions, so that they are built up, for example, as a line camera. Such sensors have a multiplicity of elements which are arranged side by side so as to form e.g. the line-shaped sensor or its illumination with a required length. Normally, such sensors or illuminations additionally have optical imaging systems. In such cases on the one hand it is desirable to perform a calibration for all the elements forming the sensor, on the other hand upon the known calibration there occurs blur, because the calibration medium does not lie in the focus area of the sensor within which the measurement of measuring objects, e.g. bank notes, is effected in the operating mode.

SUMMARY

Starting out from this prior art, the invention is based on the object to provide an apparatus and a method for the calibration of a sensor system, which with decreased effort permit a precise calibration. Furthermore, a long-time stability for the calibration is to be achieved.

The solution to these problems appears from the features of the independent claims. Developments are subject matter of the subclaims.

The invention starts out from an apparatus for the calibration of a sensor system, having at least one sensor and at least one excitation source, a control device for controlling the sensor system, a calibration medium and a drive which moves the calibration medium, controlled by the control device, into an optical path of the sensor system in a calibration mode for the calibration of the sensor system and moves the calibration medium out of the optical path of the sensor system in an operating mode for the testing of measuring objects, in particular bank notes, wherein the calibration medium has more than one reference, wherein the drive, controlled by the control device, moves the calibration medium into the optical path of the sensor system in such a way that one of the references covers a detection area of the sensor system, and the sensor system measures the reference located in the detection area, wherein the drive moves the calibration medium under the control of the control device at least one time by a predetermined stretch or a multiple of the predetermined stretch, so that another one of the references covers the detection area, and the sensor system measures the other reference located in the detection area, and wherein the predetermined stretch corresponds to an extent of the calibration medium's individual references in whose direction the drive moves the calibration medium.

The advantage of the apparatus according to the invention is that one single calibration medium with a plurality of references is sufficient for calibrating different properties of a sensor system. The use of only one calibration medium with only one drive permits a simple, compact and cost-efficient structure of the sensor system which still permits the calibration of a multiplicity of different properties of the sensor system.

In a development the sensor system is calibrated by means of a method, wherein a first calibration step is provided, in which a further calibration medium independent of the sensor system, having standardized references, is brought into a focus area of the sensor system and covers the entire detection area of the sensor system where the particular measuring object to be tested is located during the operating mode, wherein the excitation source of the sensor system excites the further calibration medium with an excitation signal, and signals successively generated by the standardized references of the further calibration medium due to the excitation signal are detected by at least one sensor of the sensor system and measuring signals are generated, and wherein an adjustment of the sensor system is effected due to the measuring signals, and a second calibration step which is performed immediately after the first calibration step, wherein the calibration medium, having non-standardized references, is brought into the optical path of the sensor system at a place which is shifted by a distance in relation to the focus area of the sensor system and covers the entire detection area of the sensor system, wherein the excitation source of the sensor system excites the calibration medium with the excitation signal, and signals successively generated by the references of the calibration medium due to the excitation signal are detected by the sensor and measuring signals are generated, and wherein the measuring signals of the second calibration step are stored, and still in the calibration mode the calibration medium is again brought into the optical path of the sensor system at the place which is shifted by the distance in relation to the focus area of the sensor system and covers the entire detection area of the sensor system, wherein the excitation source of the sensor system excites the calibration medium with the excitation signal, and signals successively generated by the references of the calibration medium due to the excitation signal are detected by the sensor and measuring signals are generated, and wherein the measuring signals of the calibration mode are compared with the stored measuring signals of the second calibration step, and an adjustment of the sensor system is effected if one or a plurality of the measuring signals of the calibration mode deviate from the stored measuring signals of the second calibration step.

The advantage of the development is that only one high-quality calibration medium having standardized references has to be used so as to permit the desired calibration. This high-quality calibration medium has to be used only once, e.g. upon the manufacturing or repair of the sensor system to be calibrated. Since this high-quality calibration medium can be used for all manufactured sensor systems, it is additionally achieved that all sensor systems of a type are equally calibrated and thus provide comparable measuring signals for a certain measuring object.

For the calibration of the sensor system in the normal operation there can be used a cost-efficient calibration medium having non-standardized references. This, moreover, has the second advantage that the high-quality calibration medium having the standardized references is not subjected to any harmful environmental influences during the operation of the sensor system, and changes of the cost-efficient calibration medium, having the non-standardized references, are taken into account upon calibrating during the operation. This allows a long-time stable calibration of the sensor system. Additionally, in the method according to the invention deviations of the calibration medium from the actual measuring place of the sensor system are taken into account, which permits a substantially more precise calibration of the sensor system which, moreover, comprises the entire detection area of the sensor system.

BRIEF DESCRIPTION OF THE DRAWINGS

Further embodiments and advantages of the invention are explained in the following with reference to the Figures and their description.

DETAILED DESCRIPTION OF VARIOUS EMBODIMENTS OF THE DISCLOSURE

Figure 1:
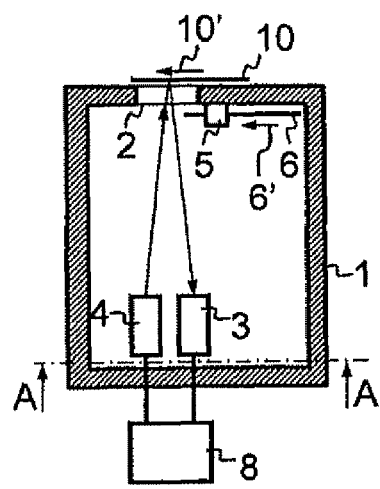
FIG. 1 shows a basic embodiment of a sensor system having a calibration medium as a sectional view, in a section perpendicular to the longitudinal axis of the sensor system.
Figure 2:
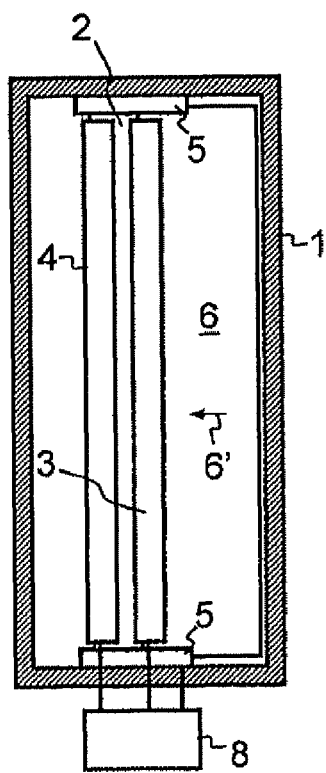
FIG. 2 shows the sensor system according to FIG. 1 as a sectional view, in a section parallel to the longitudinal axis of the sensor system, in a viewing direction A-A indicated in FIG. 1.

FIG. 1 shows a basic embodiment of a sensor system having a calibration medium as a sectional view, in a section perpendicular to the longitudinal axis of the sensor system. FIG. 2 shows the sensor system according to FIG. 1 as a sectional view, in a section parallel to the longitudinal axis of the sensor system, in a viewing direction A-A indicated in FIG. 1.

The sensor system comprises a sensor housing 1 which includes at least a sensor 3 and an excitation source 4. In the shown example the sensor 3 is a line camera which is formed by a number of detectors arranged side by side, e.g. photodiodes or by a CCD element. Likewise, two or more line cameras can be arranged in parallel side by side. The excitation source 4 is an illumination also built up in a line, which may consist of e.g. a number of elements arranged side by side such as light emitting diodes. The illumination 4 can emit for example white light, but it is also possible that illumination 4 emits light with certain spectral properties, e.g. infrared, red, green, blue, ultraviolet light etc. In the sensor housing 1 there is provided a window 2 which is transparent to the light of the illumination 4 and the light reflected back to the sensor 3. The sensor housing 1 can be formed in a dustproof manner so as to prevent a soiling of the sensor 3 or of the illumination 4. The sensor 3 and the illumination 4 are connected with a control device 8 which controls the sensor 3 and the illumination 4 and evaluates the signals of the sensor 3. The control device 8 may be formed for example by a microprocessor or a digital signal processor which may be provided with a volatile main memory and a nonvolatile memory for storing software and parameters required for the operation.

Figure 3:
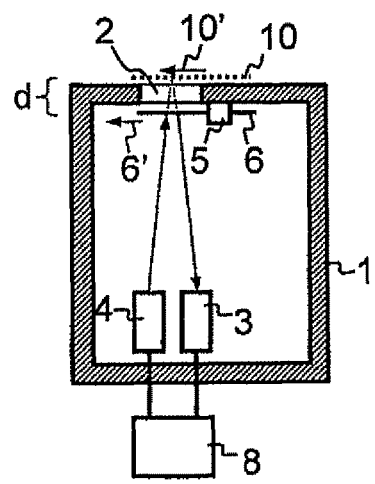
FIG. 3 shows the sensor system according to FIG. 1, after a movement of the calibration medium.

In the sensor housing 1 there is additionally located a calibration medium 6 which is connected with a drive 5, for example a linear drive. The drive 5 can move the calibration medium 6 in a first direction 6', so that the calibration medium 6 projects into the area of the window 2 as well as in the detection area of the sensor system and finally, as shown in FIG. 3, completely conceals the window 2. In this position of the calibration medium 6 the calibration of the sensor 3 is started. Basically, it is possible to start the calibration as soon as the calibration medium 6 has reached the detection area of the sensor 3, but it is preferred that the calibration does not start until after the calibration medium 6 has completely covered the area of the window 2, since in this way it is possible to prevent errors during the calibration which are caused by external interfering signals.

Figure 4:
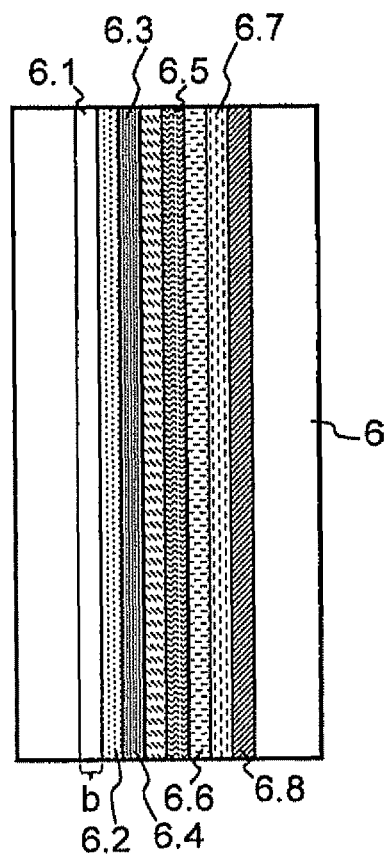
FIG. 4 shows a basic embodiment of the calibration medium shown in FIG. 1.

FIG. 4 shows a basic embodiment of the calibration medium 6 shown in FIG. 1. The calibration medium 6 has a number of strip-shaped references 6.1 to 6.8 which extend, for example, over the entire length of the calibration medium 6 and have a width b. The dimensions of the calibration medium as well as of the references 6.1 to 6.8 are set such that at least the entire detection area of the sensor 3 is covered at the place where the calibration medium 6 is brought into the optical path of the sensor 3.

Upon the calibration of the sensor 3 the calibration medium 6 is moved by the drive 5 until the first reference 6.1 is located in the optical path of the sensor 3 and covers its detection area. Thereafter, a measurement is effected for calibrating the sensor 3 by means of the first reference 6.1, for the purpose of which the illumination 4 illuminates the first reference 6.1 and the sensor 3 detects the light reflected by the first reference 6.1 and generates a measuring signal which is stored by the control device 8 e.g. in the nonvolatile memory. A measuring signal can also be generated for each of the detectors forming the sensor 3. Subsequently, the calibration medium 6 is moved by the drive 5 by a stretch b which corresponds to the width b of the references 6.1 to 6.8. In the detection area of the sensor 3 now is located the second reference 6.2 and again a measuring signal is generated by the sensor 3 and stored by the control device 8. Thereafter, the described procedure is repeated for the other references 6.3 to 6.8.

By means of the stored measuring signals of the references 6.1 to 6.8 the control device 8 calibrates the sensor 3 or the individual detectors forming the sensor 3, for the purpose of which the stored measuring signals are compared with deposited values for the particular reference 6.1 to 6.8. So as to be able to compensate for recognized deviations and to adjust the sensor system, it can be provided that the control device 8 ascertains correction factors which are stored and in later measurements of measuring objects, e.g. bank notes, are used for compensating for the present deviations. It can also be provided that in the measurements for the individual references 6.1 to 6.8 the intensity of the illumination 4 or of its individual elements is changed by the control device 8, until the deviations present in the measurements are compensated for. In so doing, the determined parameters for the illumination 4 are also stored in the nonvolatile memory of the control device 8 for later measurements. It is also possible to provide both correction factors for the measuring signals and changed intensities of the illumination 4, thus permitting a compensation for present deviations. In addition, the measuring signals of the sensor 4 or of the individual detectors can be stored for later comparisons.

The calibration medium 6 has at the beginning and end, besides the references 6.1 to 6.8, free areas which result from the above-explained requirement that the window 2 is to be concealed by the calibration medium 6, so that external interfering signals cannot negatively affect the calibration procedure. The individual references have different properties and are selected depending on the type of the sensor to be calibrated. For optical sensors it may be provided that one of the references 6.1 to 6.8 is a white reference, other references 6.1 to 6.8 may have certain spectral properties, for example infrared, red, green, blue, ultraviolet etc references. It is obvious that the number of references used can deviate from the number of eight references shown in the example in FIG. 4. Especially stable references can be formed by means of interference filters. The references 6.1 to 6.8 in this case are formed e.g. by multi-layer interference filters which block or let pass certain wavelengths or wavelengths ranges. When the references 6.1 to 6.8 are to be used for measurements in remission, the interference filter or interference filters can be applied onto a reflecting carrier material.

It is also obvious that in the above-described calibration procedure not all references 6.1 to 6.8 have to be used, or that not upon each calibration all references 6.1 to 6.8 are used. In this case, the calibration medium 6 is moved by the drive 5 between the measurements made for the individual references 6.1 to 6.8 by stretches which are multiples of the width b of the references 6.1 to 6.8. In case the individual references 6.1 to 6.8 do not directly adjoin each other, of course, the distance between them has to be taken into account upon the determination of the width b. The same applies to different widths b of the individual references 6.1 to 6.8.

Deviating from the above-described embodiment, the calibration medium 6 as well as the drive 5 can be differently realized, so that the calibration medium 6 is brought into and removed from the optical path of the sensor 3 e.g. by rotating, tilting, swiveling, pushing, drawing etc. In general, translatory or rotatory movements or composed movements are possible. It has to be particularly observed here that the respective drive moves the calibration medium 6 in such a way that the individual references 6.1 to 6.8 for the individual measurements are positioned exactly in the detection area of the sensor 3, i.e. are moved in each case by the width b of the respective reference 6.1 to 6.8.

If for the calibration of the sensor system the above-described calibration medium 6 is to be realized cost-effectively, i.e. in particular without standardized references 6.1 to 6.8, a preceding calibration with a further calibration medium 6.8 having standardized references is required. For this purpose, in a first calibration step a further calibration medium 10 (FIG. 1) is brought into the detection area of the sensor system 10'. This can be effected for example by an operator, but it is also possible that the further calibration medium 10 is brought in by a transport system, which e.g. is component of a bank note processing machine in which the sensor system is mounted and used for testing bank notes.

The further calibration medium 10 here is positioned such that it is located in the focus area of the sensor system, i.e. at a place where are also located the measuring objects to be examined during an operating mode, e.g. bank notes in the bank note processing machine. The further calibration medium 10 here is dimensioned such that it covers the entire detection area of the sensor system. That is, it has in particular a length which corresponds to a length of the sensor 3, such as shown e.g. in FIG. 2, or to the length of its optical detection area. Advantageously, the further calibration medium 10 is designed so large that it covers the entire window 2. Thus preventing that the calibration by means of the further calibration medium 10 is influenced by external interfering signals. The further calibration medium 10 has high-quality, standardized references which in their properties basically correspond to the properties of the references 6.1 to 6.8 of the previously described calibration medium 6. The references 6.1 to 6.8 of the calibration medium 6, however, in contrast to the references of the further calibration medium 10, are non-standardized. Likewise, it is possible that the calibration medium 6 is provided with a reference which has properties which are at least similar to the properties of the reference of the further calibration medium 10. If one of the references of the further calibration medium 10 is a white reference, for example for the calibration medium 6 there can be used a reference which is white or relatively bright. Ideally, the properties of the references of the calibration medium 6 should have a good ageing stability.

Controlled by the control device 8, in the first calibration step the further calibration medium 10 is illuminated with the illumination 4 and the light reflected by the further calibration medium 10 is detected successively for all references by the sensor 3. The measuring signals of the sensor 3, for example for the intensity of the light reflected by the further calibration medium 10, are analyzed by the control device 8. Starting out from the further calibration medium 10 used having the standardized references and their thus exactly defined properties, an adjustment of the sensor system can be effected, when the intensities for the references measured by the sensor 3 do not correspond to the intensities expected due to the known properties of the further calibration medium 10 used. Since the further calibration medium 10 extends over the entire sensor 3, for all detectors of the sensor 3 there are generated measuring signals which permit the calibration of the respective detectors. For adjusting the sensor system for example correction factors can be calculated which compensate for deviations present upon the calibration of the sensor system with the first calibration medium 10. The correction factors are stored in the nonvolatile memory of the control unit 8 and used in later measurements for generating the measuring signals. It can also be provided that the intensity of the illumination 4 or of its individual elements is changed by the control device 8, until the deviations present in the measurement are compensated for. In so doing, the determined parameters for the illumination 4 are also stored in the nonvolatile memory of the control device 8 for later measurements. Likewise, it is possible to provide both correction factors for the measuring signals and changed intensities of the illumination 4, thus permitting a compensation for present deviations. At the end of the first calibration step, in addition, the measuring signals of the sensor 4 or of the individual detectors can be stored for later comparisons.

Advantageously, it is provided that the first calibration step is performed only once, e.g. upon the manufacturing or after a repair of the sensor system, so that only for the first calibration step a further calibration medium 10 having the standardized references has to be provided.

Immediately after the first calibration step, a second calibration step is performed with the sensor system adjusted in the first calibration step. For this, the calibration medium 6 present within the sensor housing 1 is used, which has references 6.1 to 6.8 with, likewise, defined properties. But, as it will be explained in the following, one can do without the use of standardized and thus expensive references within the sensor system as a component of the calibration medium 6.

For the second calibration step, as indicated in FIG. 1 and shown in FIG. 3, the calibration medium 6 is brought into the optical path of the sensor 3 by the drive 5.

In the second calibration step an illumination of the calibration medium 6 or its references 6.1 to 6.8 is effected by the illumination 4. If, as described above for the first calibration step, the intensity of the illumination 4 was changed for the adjustment, the illumination is operated with this changed intensity. The light reflected by the calibration medium 6 is detected by the sensor 3 or the individual detectors and for the individual references 6.1 to 6.8 successively converted into corresponding measuring signals, for example for the intensity of light reflected from the calibration medium 6. While in the above-described first calibration step there were determined and stored correction factors, these are used upon the generation of the measuring signals by the control device 8. The measuring signals of the sensor 3 or of the individual detectors for the calibration medium 6 are stored by the control device 8 in its nonvolatile memory at the end of the second calibration step for the references 6.1 to 6.8.

The measuring signals of the second calibration step normally will differ from the measuring signals of the first calibration step, because these measuring signals on the one hand express that not the further calibration medium 10 having the standardized references is used. On the other hand, it becomes noticeable that the calibration medium 6 for the measurement is not arranged outside the sensor housing 1 in the focus area of the sensor 3 like the further calibration medium 10 as indicated by dashed lines in FIG. 3, but moved by a distance d into the sensor housing 1 and thus is located by the distance d outside the focus area of the sensor system or of the sensor 3 and/or of the illumination 4. Since the second calibration step is performed immediately after the first calibration step, the measuring signals of the second calibration step represent a basis for later calibrations and adjustments of the sensor system or of the sensor 3 and/or of the illumination 4 during the normal operation. The basically disadvantageous deviations of the non-standardized properties of the calibration medium 6 as well as the basically disadvantageous moving of the calibration medium 6 by the distance d out from the focus area of the sensor 3 or of the illumination 4 thus are automatically included, and so they are also automatically taken into account upon later calibrations with the calibration medium 6 or its references 6.1 to 6.8 and cannot negatively affect the calibration procedure. Moreover, e.g. changes of the calibration medium 6 or its references 6.1 to 6.8 due to ageing thus cannot falsely affect later calibration processes, since these always cause changed measuring signals which are compensated for upon the calibration.

For the operating mode, the reference medium 6 is removed from the optical path of the sensor 3 or of the illumination 4 under the control of the control device 8 by the drive 5. During the operating mode, then there are brought in measuring objects, e.g. bank notes, at the place for the further reference medium 10 shown in FIG. 1a. For this purpose, for example a transport system of a bank note processing machine can be used, in which the sensor system is used for testing bank notes. Upon the evaluation of the measuring signals of the sensor 3 by the control device 8, for testing bank notes in the operating mode the above-described correction factors and/or the changed intensity of the illumination 4 are used.

After predetermined periods of use of the sensor system or upon switching on the sensor system or the bank note processing machine having the sensor system it can be provided that a re-calibration and re-adjustment of the sensor system or of the sensor 3 and/or of the illumination 4 is performed in a calibration mode. For this purpose, like in the above-described second calibration step, the calibration medium 6 is brought into the optical path of the sensor 3 and/or of the illumination 4 by the drive 5. The measuring signals of the sensor 3 or of the individual detectors for the references 6.1 to 6.8 ascertained upon the re-calibration are compared with the measuring signals of the second calibration step stored in the nonvolatile memory of the control device 8. If deviations occur, the sensor system, i.e. the sensor 3 and/or the illumination 4, is adjusted in the way described above for the first calibration step. For this purpose, correction factors for correcting the deviations of the measuring signals are ascertained and/or the intensity of the illumination 4 or of its individual elements is changed. The correction factors or the change of the intensity of the illumination 4 are stored in the nonvolatile memory of the control device 8 and are subsequently used in the operating mode, for which the calibration medium 6, under the control of the control device 8 by the drive 5, again is removed from the optical path of the sensor 3.

The deviations ascertained upon the re-calibration between the measuring signals ascertained upon the calibration and the measuring signals of the second calibration step stored in the nonvolatile memory of the control device 8, moreover, allow a statement about certain drift phenomena of the sensor system, i.e. changes of sensor 3, illumination 4, second calibration medium 6 etc due to ageing, soiling, etc.

In the above-described embodiments there is shown a sensor 3 measuring in reflection with associated illumination 4. But it is obvious that a sensor measuring in transmitted light can also be calibrated with an illumination located opposite the sensor outside the sensor housing 1. For this, the calibration media 6, 10 as well as their references have to be chosen accordingly, in particular these have to be transparent to at least a part of the light of the illumination 4. It is obvious that, besides the described optical sensors, other sensors can be calibrated with the proposed method, when calibration media 6, 10 and their references with appropriate sensor-specific properties are chosen.

In the above description there was explained by way of example, that the adjustment of the sensor system due to the deviations ascertained upon the calibration can be effected by means of correction factors and/or a change of the intensity of the excitation source. The adjustment of the sensor system, i.e. the correction of the ascertained deviations, however, can also be achieved in other ways. For example, the amplification of amplifiers can be changed, with which the measuring signals coming from the sensor or the individual detectors are amplified for the further processing.

The invention claimed is:

1. A method for the calibration of a sensor system comprising at least one sensor, at least one excitation source, a control device arranged to control the sensor system, a first calibration medium and a drive arranged to move the first calibration medium under the control of the control device into an optical path of the sensor system in a calibration mode of the calibration of the sensor system and to move the first calibration medium out of the optical path of the sensor system in an operating mode for the testing of measuring objects, wherein the method comprises the steps of:

during a first calibration step, moving a second calibration medium independent of the sensor system, having standardized references, into a focus area of the sensor system so that the second calibration medium covers an entire detection area of the sensor system where a particular measuring object to be tested is located during the operating mode; exciting the second calibration medium with an excitation signal from the excitation source of the sensor system so that signals are successively generated by the standardized references of the second calibration medium due to the excitation signal and are detected by at least one sensor of the sensor system to generate measuring signals; and adjusting the sensor system due to the measuring signals;

during a second calibration step, which is performed immediately after the first calibration step, bringing the first calibration medium, having non-standardized references, into the optical path of the sensor system at a place which is shifted by a distance (d) in relation to the focus area of the sensor system, so that the first calibration medium covers the entire detection area of the sensor system; exciting the first calibration medium with the excitation signal from the excitation source of the sensor system so that signals are successively generated by the references of the first calibration medium due to the excitation signal being detected by the sensor to generate measuring signals; and storing the measuring signals of the second calibration step; and during the calibration mode, bringing the first calibration medium into the optical path of the sensor system at the place which is shifted by the distance (d) in relation to the focus area of the sensor system so that the first calibration medium covers the entire detection area of the sensor system; exciting the first calibration medium with the excitation signal from the excitation source of the sensor system to generate signals successively by the references of the first calibration medium due to the excitation signal being detected by the sensor to generate measuring signals; comparing the measuring signals of the calibration mode with the stored measuring signals of the second calibration step; and adjusting the sensor system if one or a plurality of the measuring signals of the calibration mode deviate from the stored measuring signals of the second calibration step, wherein the first calibration medium comprises more than one reference and wherein the drive is arranged to move the first calibration medium into the optical path of the sensor system in such a way that one of the references covers a detection area of the sensor system to enable the sensor system to measure the reference located in the detection area at least one time by a predetermined stretch (b) or a multiple of the predetermined stretch, so that another one of the references covers the detection area to enable the sensor system to measure the other reference located in the detection area, and wherein the predetermined stretch (b) corresponds to an extent of the first calibration mediums' individual references in whose direction the drive moves the first calibration medium.

2. The method according to claim 1, wherein the references of the first calibration medium and the references of the second calibration medium have comparable properties.

3. The method according to claim 1, wherein the calibration and adjustment of the sensor are effected for a multiplicity of detectors forming the sensor and for each detector measuring signals are generated and stored.

4. The method according to claim 1, wherein adjusting the sensor system further comprises the step of determining correction factors; and compensating for any deviation in the measuring signals in later measurements of measuring objects using the correction factors.

5. The method according to claim 1, wherein adjusting the sensor system further comprises the step of changing an intensity of the excitation signal of the excitation source based on the measuring signals.

* * * * *